United States Patent
Lu et al.

(10) Patent No.: US 9,278,939 B2
(45) Date of Patent: Mar. 8, 2016

(54) METHODS FOR PREPARATION OF (4,6-DIHALO-PYRIMIDIN-5-YL)-ACETALDEHYDES

(71) Applicant: SUZHOU JONATHAN NEW MATERIAL TECHNOLOGY CO., LTD., Jiangsu (CN)

(72) Inventors: Shaopo Lu, Jiangsu (CN); Zhuocai Li, Jiangsu (CN)

(73) Assignee: SUZHOU JONATHAN NEW MATERIAL TECHNOLOGY CO., LTD., Jiangsu (CN)

( * ) Notice: Subject to any disclaimer, the term of this patent is extended or adjusted under 35 U.S.C. 154(b) by 0 days.

(21) Appl. No.: 14/762,963

(22) PCT Filed: Dec. 6, 2013

(86) PCT No.: PCT/CN2013/088796
§ 371 (c)(1),
(2) Date: Jul. 23, 2015

(87) PCT Pub. No.: WO2015/039387
PCT Pub. Date: Mar. 26, 2015

(65) Prior Publication Data
US 2015/0368206 A1    Dec. 24, 2015

(30) Foreign Application Priority Data

Sep. 18, 2013 (CN) .......................... 2013 1 0429240

(51) Int. Cl.
*C07D 239/30* (2006.01)
(52) U.S. Cl.
CPC .................................. *C07D 239/30* (2013.01)

(58) Field of Classification Search
CPC ..................................................... C07D 239/30
See application file for complete search history.

(56) References Cited

FOREIGN PATENT DOCUMENTS

| | | |
|---|---|---|
| CN | 102159572 A | 8/2011 |
| CN | 103524423 A | 1/2014 |
| CN | 103554035 A | 2/2014 |
| WO | WO 03105770 A2 | 12/2003 |

*Primary Examiner* — Bruck Kifle
(74) *Attorney, Agent, or Firm* — Muncy, Geissler, Olds & Lowe, P.C.

(57) ABSTRACT

This invention relates to the synthesis of chemical compounds and particularly to methods for the preparation of (4,6-dihalo-pyrimidin-5-yl)-acetaldehydes. The methods involve preparing a compound of the following general formula V from a compound of the following general formula IV through hydrolysis under the action of mercury dichloride and calcium carbonate, according to the following equation:

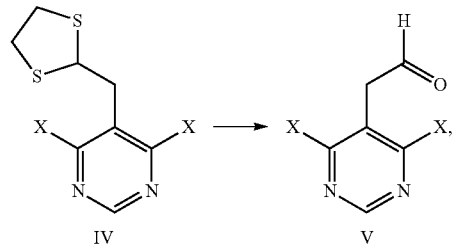

wherein X is Cl or Br. The methods offer the benefits of use of highly available materials, high step yields, moderate reaction conditions, simply post-processing and purification, and suitability to industrialized production.

10 Claims, No Drawings

METHODS FOR PREPARATION OF (4,6-DIHALO-PYRIMIDIN-5-YL)-ACETALDEHYDES

TECHNICAL FIELD

The present invention relates to the synthesis of chemical compounds and, in particular, to methods for preparing (4,6-dihalo-pyrimidin-5-yl)-acetaldehydes.

BACKGROUND

G protein-coupled receptor 119 (GPR119) is a new diabetes drug target. GPR119 agonists have been the focus of new drug development efforts of many multinational pharmaceutical companies. Among a series of small-molecule GPR119 agonists developed by GlaxoSmithKline, GSK252A of the following formula has the most outstanding performance:

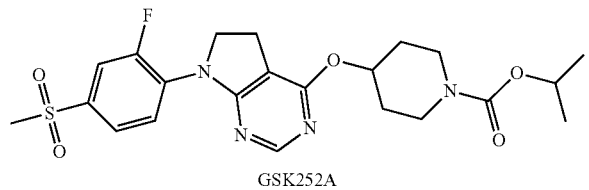 [SMILES: CC(C)OC(=O)N1CCC(Oc2ncnc3c2CCN3c2ccc(S(C)(=O)=O)cc2F)CC1]

GSK252A

The GSK252A molecule includes a novel pyrrolopyrimidine bicyclic structure. One important method of constructing such a bicyclic structure is a ring-closing reaction using (4,6-dichloro-pyrimidin-5-yl)-acetaldehyde. Therefore, the synthesis of (4,6-dichloro-pyrimidin-5-yl)-acetaldehyde is of remarkable importance to the subsequent development of GSK252A and other similar active substances based on the pyrrolopyrimidine bicyclic structure.

Current synthesis of (4,6-dichloro-pyrimidin-5-yl)-acetaldehyde, the compound of the following formula I, relies mainly on an oxidation reaction for creating an oxoethyl group in position 5. One example of this approach is disclosed in WO2010/9195, in which the synthesis is based on the compound of the following formula II and uses potassium osmate as an oxidant, according to the following equation:

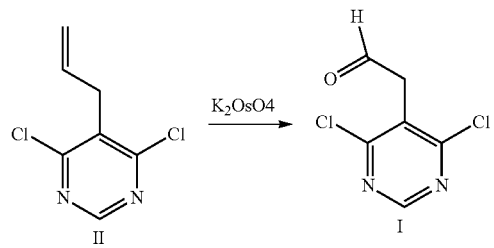

WO2003/105770 discloses the synthesis from the compound of the following formula III, in which osmium tetroxide is used as an oxidant, according to the following equation:

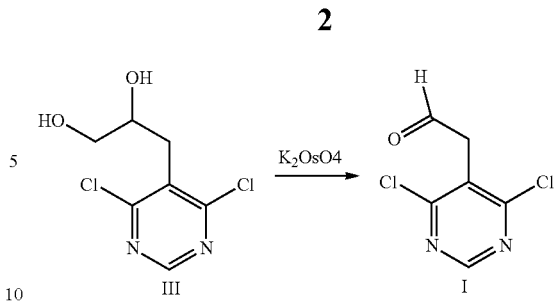

However, oxidation reactions are generally associated with a high risk and low controllability and thus have unsatisfactory final yields. In addition, osmium tetroxide and potassium osmate are not suitable for use in the production of pharmaceutical intermediates and industrialized production because they are less water soluble, creates difficulties in post-processing, and tends to remain in the final products.

SUMMARY OF THE INVENTION

The present invention seeks to overcome the deficiencies of the existing (4,6-dichloro-pyrimidin-5-yl)-acetaldehyde preparation methods, i.e., being unsuitable for industrialized production and detrimental to environmental protection, by presenting methods of preparing (4,6-dihalo-pyrimidin-5-yl)-acetaldehydes.

To this end, in the method of preparing a (4,6-dihalo-pyrimidin-5-yl)-acetaldehyde according to the present invention, a compound of the following general formula V is produced from a compound of the following general formula IV through hydrolysis under the action of mercury dichloride and calcium carbonate, according to the following equation:

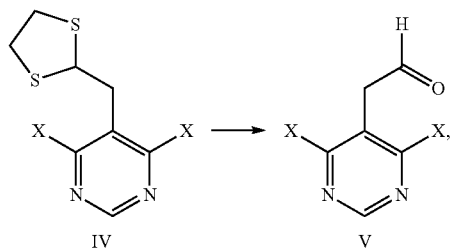

wherein, X is Cl or Br.

Preferably, the hydrolysis is conducted in a solvent which is a mixture of an organic solvent and water, the organic solvent is acetone, acetonitrile or tetrahydrofuran, and the organic solvent is present in a volume ratio of from 2:1 to 5:1 to the water.

Preferably, the mercury dichloride is present in a molar ratio of 1.5:1 to 2.5:1 to the compound of the general formula IV.

Preferably, the compound of the general formula IV is obtained from the halogenation of 5-[(1,3-dithiolan-2-yl)methyl]-4,6-dihydroxypyrimidine of the following formula VI, according to the following equation:

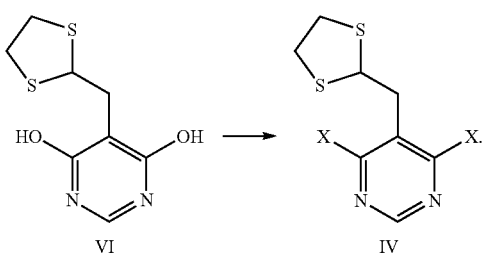

Preferably, the halogenation is conducted in the presence of a halogenating agent which is phosphorus oxychloride, phosphorus oxybromide, oxalyl chloride or thionyl chloride.

Preferably, the compound of the formula VI is obtained from a ring-closing reaction of a compound of the following general formula VII and formamidine acetate in the presence of an alkaline agent, according to the following equation:

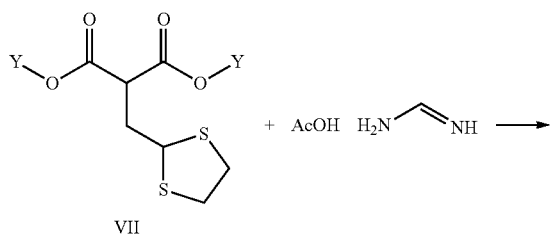

wherein, Y is independently selected from $C_1$-$C_4$ alkyls.

Preferably, the alkaline agent is selected from sodium ethoxide, potassium ethoxide, sodium methoxide or potassium methoxide.

Preferably, the ring-closing reaction is carried out in a solvent of a $C_1$-$C_4$ alcohol.

Preferably, the compound of the general formula VII is obtained from a substitution reaction of a malonate diester and 2-(chloromethyl)-1,3-dithiolane, according to the following equation:

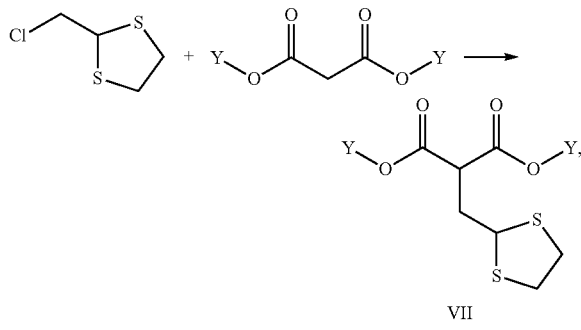

wherein, Y is independently selected from $C_1$-$C_4$ alkyls.

Preferably, the 2-(chloromethyl)-1,3-dithiolane is obtained from the condensation of 1,2-ethanedithiol with 2-chloro-1,1-dimethoxyethane.

The methods according to the present invention offer the benefits of use of highly available materials, high step yields, moderate reaction conditions, simply post-processing and purification, and suitability to industrialized production.

DETAILED DESCRIPTION OF THE EXEMPLARY EMBODIMENTS

The present invention will be described in greater detail with reference to the following several examples which are provided merely for more detailed description of the preferred embodiments of the invention rather than for limiting the subject matters of the invention. The objects of the present invention are attained by each of the subject matters thereof. In other words, each of the temperatures or reagents provided in the following examples can be substituted by a corresponding temperature or reagent presented above, with the objects of the invention being still achieved.

In the following examples:

NMR measurements were performed using a Bruker 400 MHz instrument, in which TMS served as an internal standard and ppm as a measurement unit for chemical shifts.

In addition, all the reagents used in the examples were commercially available.

EXAMPLE 1

Preparation of 2-(chloromethyl)-1,3-dithiolane

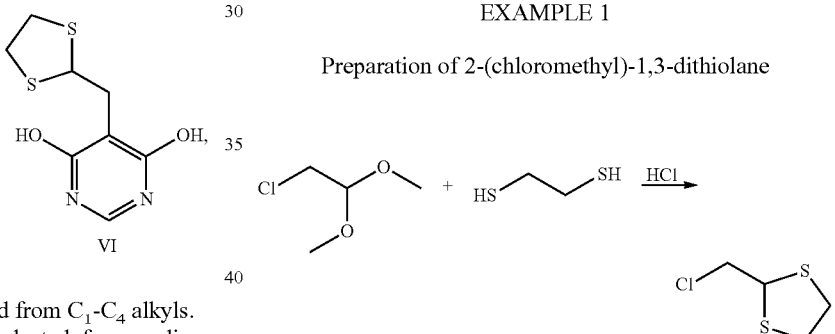

Ethanedithiol (33.4 g, 0.35 mol) and 50 mL of concentrated hydrochloric acid were successively added in a reaction flask of 250 mL. The whole was chilled to 0° C. and 2-chloro-1,1-dimethoxyethane (48.7 g, 0.39 mol) was then added slowly dropwise. With the addition completed, the mixture was warmed up to room temperature. After 5 hours of reaction, 100 ml of water was added and the organic phase was extracted thrice with dichloromethane, washed with an aqueous solution saturated with sodium bicarbonate and then dried. After solvent removal and evaporation, 45 g of 2-(chloromethyl)-1,3-dithiolane was obtained with a yield of 81%.

EXAMPLE 2

Preparation of 2-[(1,3-dithiolan-2-yl)methyl]-diethyl Malonate (Compound of the Formula VII-1)

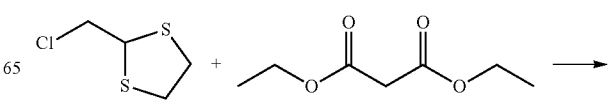

-continued

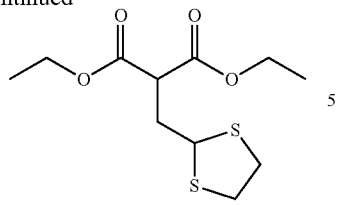

VII-1

Potassium carbonate (153 g, 1.1 mol) was added to 500 mL of acetone. The mixture was stirred, during which potassium iodide (12.2 g, 0.075 mol) and 2-(chloromethyl)-1,3-dithiolane (114.4 g, 0.74 mol) were added and, subsequently, dropwise addition of diethyl malonate (118.4 g, 0.74 mol) began 5 minutes later than the beginning of the stirring. With the addition completed, the whole was heated to 50° C. and then left at this temperature for 24 hours. The reaction was then suction filtered and the filter cake was washed thrice with acetone. The filtrate together with the washing acetone was subjected to solvent removal in order to obtain a yellowish oil of 175.4 g with a yield of 85%. $^1$HNMR (400 MHz, CDCl$_3$) δ: 4.2 (m, 4H); 3.8 (s, 1H); 3.1 (s, 1H); 2.5-2.9 (m, 4H); 1.24~1.29 (m, 6H).

EXAMPLE 3

Preparation of 5-[(1,3-dithiolan-2-yl)methyl]-4,6-dihydroxypyrimidine (Compound of the Formula VI)

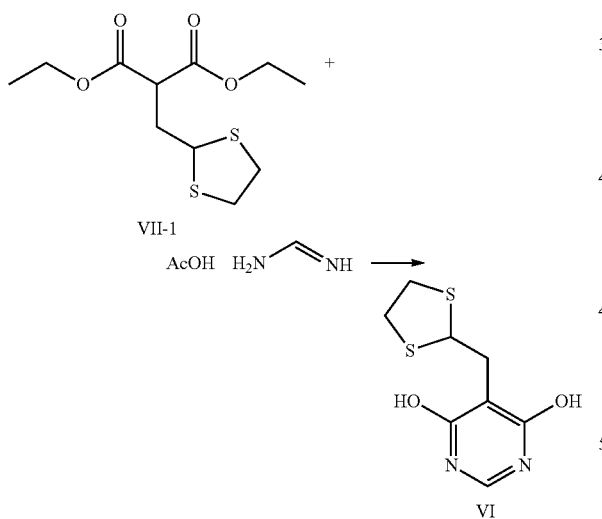

150 mL of anhydrous alcohol was added in a reaction flask and then cooled to 0° C. Then were added sodium ethoxide (21 g, 0.31 mol) in several batches and 2-[(1,3-dithiolan-2-yl)methyl]-diethyl malonate (compound of the formula VII-1, 28.6 g, 0.103 mol) dropwise. With the dropwise addition completed, formamidine acetate (11 g, 0.103 mol) was further added. The whole was then heated to 60° C. and left at the temperature for 3 hours. After the reaction, the alcohol was removed and 200 mL of water was added. A 6N HCl solution was used to adjust the pH to 2 to cause a solid precipitate which was subsequently filtered by suction and dried to obtain the hydrochloride of 5-[(1,3-dithiolan-2-yl)methyl]-4,6-dihydroxypyrimidine as a yellowish solid of 17 g with a yield of 74%. $^1$HNMR (400 MHz, CD$_3$OD) δ: 8.2 (s, 1H); 4.0 (t, 1H); 3.2 (d, 2H); 2.5-2.9 (m, 4H).

EXAMPLE 4

Preparation of 5-[(1,3-dithiolan-2-yl)methyl]-4,6-dichloropyrimidine (Compound of the Formula IV-1)

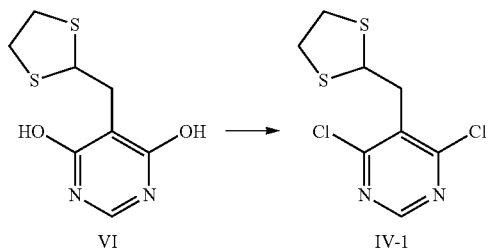

50 mL of phosphorus oxychloride was added in a reaction flask and then cooled to 0° C. 5-[(1,3-dithiolan-2-yl)methyl]-4,6-dihydroxypyrimidine (compound of the formula VI, 15 g, 0.065 mol) was slowly added with stirring. Afterward, the mixture was slowly heated to 90° C. and maintained at the temperature for 6 hours. The reaction was poured into 300 mL of iced water and the organic phase was extracted thrice with dichloromethane. The obtained organic phase was dried and subjected to solvent removal, resulting in a yellow solid. The solid was then recrystallized in ethyl acetate and petroleum ether (1:1) in order to obtain a yellowish solid of 16.1 g with a yield of 92.5%. $^1$HNMR (400 MHz, CDCl$_3$) δ: 9.7 (s, 1H); 4.1 (t, 1H); 3.2 (d, 2H); 2.5-2.9 (m, 4H).

EXAMPLE 5

Preparation of (4,6-dichloro-pyrimidin-5-yl)-acetaldehyde (Compound of the Formula V-1)

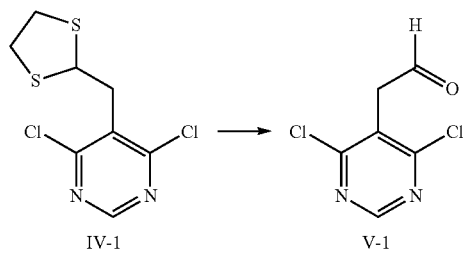

5-[(1,3-dithiolan-2-yl)methyl]-4,6-dichloropyrimidine (compound of the formula IV-1, 13.4 g, 0.05 mol) was added to 200 mL of a 4:1 mixture of acetonitrile and water, and mercury dichloride (27.1 g, 0.1 mol) and calcium carbonate (10 g, 0.1 mol) were then further added with stirring. After 6 hours of reaction at the room temperature, suction filtration was carried out. The solid was washed with acetonitrile and then the combined filtrate was subjected to solvent removal, followed by the addition of 200 mL of dichloromethane. The organic phase was then washed with an aqueous solution saturated with sodium bicarbonate, dried and subjected to solvent removal, resulting in a yellow solid. The solid was then recrystallized in ethyl acetate and petroleum ether (1:1)

in order to obtain a yellowish solid of 8.3 g with a yield of 87%. $^1$HNMR (400 MHz, CDCl$_3$) δ: 9.80 (s, 1H), 8.74 (s, 1H), 4.14 (s, 2H).

What is claimed is:

1. A method for preparing a (4,6-dihalo-pyrimidin-5-yl)-acetaldehyde, comprising preparing a compound of formula V from a compound of formula IV through hydrolysis under an action of mercury dichloride and calcium carbonate, according to the following equation:

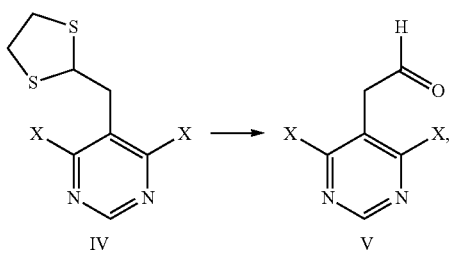

wherein, X is Cl or Br.

2. The method for preparing a (4,6-dihalo-pyrimidin-5-yl)-acetaldehyde according to claim 1, wherein the hydrolysis is conducted in a solvent which is a mixture of an organic solvent and water, wherein: the organic solvent is acetone, acetonitrile or tetrahydrofuran, and the organic solvent is present in a volume ratio of 2:1 to 5:1 to the water.

3. The method for preparing a (4,6-dihalo-pyrimidin-5-yl)-acetaldehyde according to claim 1, wherein the mercury dichloride is present in a molar ratio of 1.5:1 to 2.5:1 to the compound of the general formula IV.

4. The method for preparing a (4,6-dihalo-pyrimidin-5-yl)-acetaldehyde according to claim 1, wherein the compound of the general formula IV is obtained from halogenation of 5-[(1,3-dithiolan-2-yl)methyl]-4,6-dihydroxypyrimidine of the following formula VI, according to the following equation:

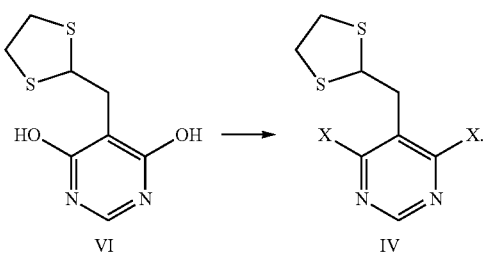

5. The method for preparing a (4,6-dihalo-pyrimidin-5-yl)-acetaldehyde according to claim 4, wherein the halogenation is conducted in the presence of a halogenating agent which is phosphorus oxychloride, phosphorus oxybromide, oxalyl chloride or thionyl chloride.

6. The method for preparing a (4,6-dihalo-pyrimidin-5-yl)-acetaldehyde according to claim 4, wherein the compound of the formula VI is obtained from a ring-closing reaction of a compound of formula VII and formamidine acetate in the presence of an alkaline agent, according to the following equation:

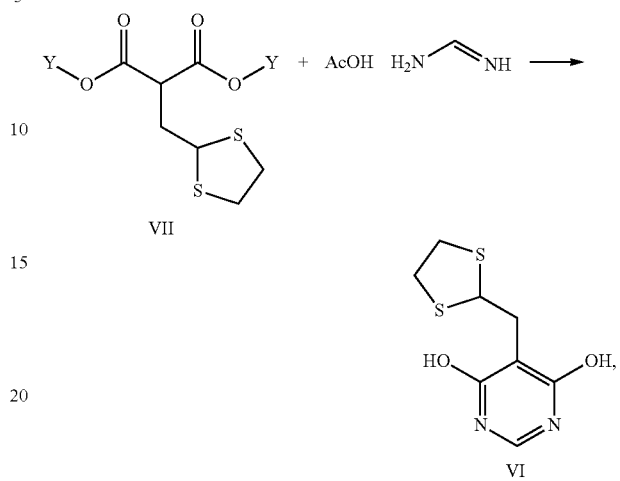

wherein, Y is independently selected from $C_1$-$C_4$ alkyls.

7. The method for preparing a (4,6-dihalo-pyrimidin-5-yl)-acetaldehyde according to claim 6, wherein the alkaline agent is selected from sodium ethoxide, potassium ethoxide, sodium methoxide or potassium methoxide.

8. The method for preparing a (4,6-dihalo-pyrimidin-5-yl)-acetaldehyde according to claim 6, wherein the ring-closing reaction is carried out in a solvent of a $C_1$-$C_4$ alcohol.

9. The method for preparing a (4,6-dihalo-pyrimidin-5-yl)-acetaldehyde according to claim 6, wherein the compound of formula VII is obtained from a substitution reaction of a malonate diester and 2-(chloromethyl)-1,3-dithiolane, according to the following equation:

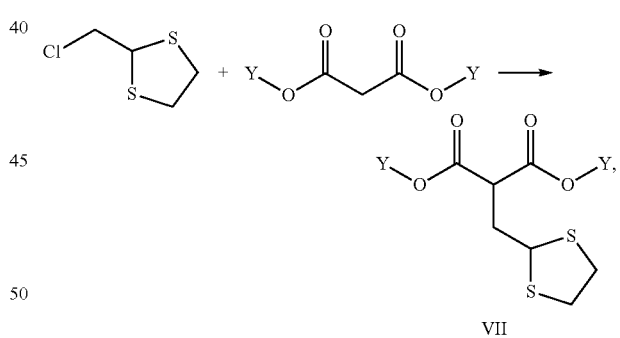

wherein, Y is independently selected from $C_1$-$C_4$ alkyls.

10. The method for preparing a (4,6-dihalo-pyrimidin-5-yl)-acetaldehyde according to claim 9, wherein the 2-(chloromethyl)-1,3-dithiolane is obtained from condensation of 1,2-ethanedithiol with 2-chloro-1,1-dimethoxyethane.

* * * * *